(12) United States Patent
Vrijheid et al.

(10) Patent No.: US 6,993,373 B2
(45) Date of Patent: Jan. 31, 2006

(54) INVASIVE DEVICE PROVIDED WITH A SEGMENTED ELECTRICAL CONNECTION CONDUCTOR

(75) Inventors: Johan Ernst Willy Vrijheid, Eindhoven (NL); Johannes Jacobus Van Vaals, Eindhoven (NL)

(73) Assignee: Koninklijke Philips Electronics, N.V., Eindhoven (NL)

( * ) Notice: Subject to any disclaimer, the term of this patent is extended or adjusted under 35 U.S.C. 154(b) by 703 days.

(21) Appl. No.: 09/990,208

(22) Filed: Nov. 21, 2001

(65) Prior Publication Data

US 2002/0095084 A1    Jul. 18, 2002

(30) Foreign Application Priority Data

Nov. 24, 2000  (EP) ................................. 00204189

(51) Int. Cl.
*A61B 5/055*  (2006.01)
(52) U.S. Cl. ..................... 600/411; 128/897; 174/126.1
(58) Field of Classification Search ................ 600/407, 600/411, 422–423; 128/897; 174/70 R, 174/68.1, 126.1; 324/318, 322

See application file for complete search history.

(56) References Cited

U.S. PATENT DOCUMENTS 5,294,886 A    3/1994  Duerr .......................... 324/318
5,916,162 A    6/1999  Snelten et al. .............. 600/411

OTHER PUBLICATIONS

Glowinski et al: "Catheter Visualization Using Locally Induced Actively Controlled Field Inhomogeneities," Magnetic Resonance In Medicine, Academic Press, Duluth, MN, US, vol. 38, No. 2, Jan. 8, 1997, pp. 253-258.

*Primary Examiner*—Ruth S. Smith

(57) ABSTRACT

An invasive device 17, such as a catheter, is connected to a supply and control unit via a connection conductor 21 for the transfer of power supply energy and/or LF signals to and from an electrical circuit 20 in the distal part 18 of the device. During operation the connection conductor traverses the homogeneous magnetic field and the RF field of the MRI apparatus; this may give rise to heating of the connection conductor and/or to a disturbance of said fields. In order to mitigate these drawbacks, the connection conductor in accordance with the invention is subdivided into mutually separated segments 22-$i$, each of which is much shorter (for example, $1/20$) than the wavelength of the RE field in the apparatus; the segments are separated from one another by separating elements 23-$i$ (self-inductances) that provide a high inductance for said RF frequencies and a low inductance for comparatively low frequencies.

7 Claims, 2 Drawing Sheets

INVASIVE DEVICE PROVIDED WITH A SEGMENTED ELECTRICAL CONNECTION CONDUCTOR

Figure 1:
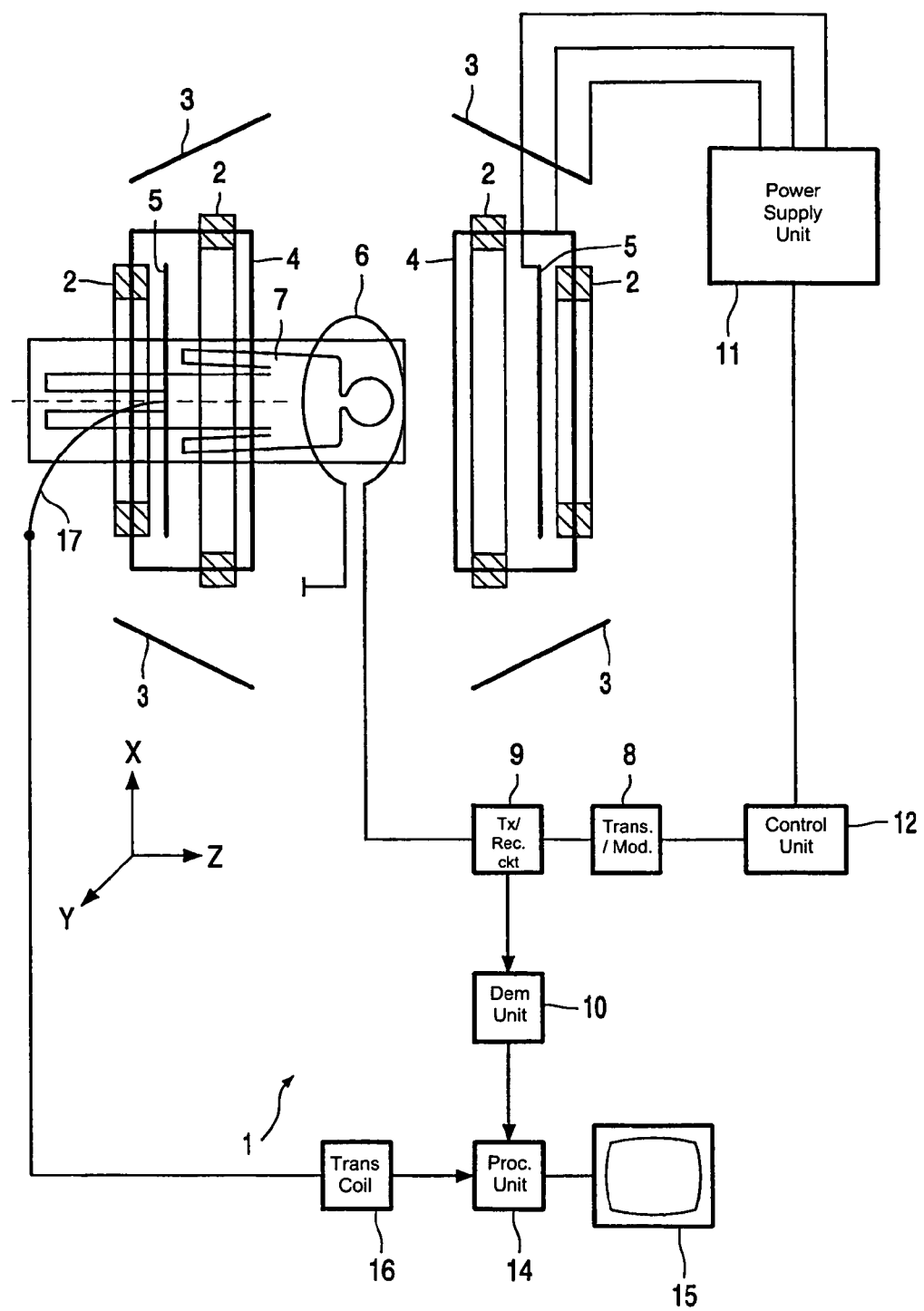

The invention relates to an invasive device that is intended to be introduced into an object that is to be imaged by means of an MRI apparatus, which invasive device has a distal end and is provided with a housing that is connected thereto, with a circuit that is arranged at the area of the distal end, and also with an electrical connection conductor that is connected to the circuit and extends through the housing.

A device of this kind is known from U.S. Pat. No. 5,916,162. As is customary in the case of a medical MRI apparatus, the object that is to be imaged by means of the MRI apparatus disclosed in the cited patent is a part of the body of a patient. For numerous medical examinations or interventions it is desirable to introduce a device into the body of the patient, for example, a catheter, a laparoscope or a biopsy needle. Such a device can be guided to an internal organ via an existing opening in the body or via an opening that is especially created for this purpose, for example, in an artery. The device has an elongate shape where a distal end that forms one unit with a usually hollow housing whereby the distal end is advanced through the body opening during operation. In or on the distal end there may be provided an (electrical) circuit for treatment or observation of the inside of the patient. After its introduction, the attendant physician can no longer directly observe the location of said distal end, even though in such cases it is very important to know where the end of the device is situated in the body of the patient.

The cited U.S. Pat. No. 5,916,162 describes an invasive device that is suitable for use in conjunction with imaging by means of an MRI apparatus. The patient is imaged by the MRI apparatus while the invasive device is present within the body. In order to make the device visible, it is provided with a circuit in the form of an RF coil that is arranged at the distal end and is connected, via an electrical connection conductor that extends through the housing, to a processing unit for processing signals that are received by the RF coil. The position of the RF coil can be determined on the basis of the nature of the magnetic resonance signals received. This position is subsequently superposed on an image that is to be formed by means of the MRI apparatus and can be displayed on a monitor.

Because the electrical connection conductor that extends through the housing is situated in the RF field of the MRI apparatus, it is subject to heating; this is annoying to the patient to be examined. In order to counteract such heating, the connection conductor in the known invasive device is accommodated in a hollow carrier, the outer side of which is provided with a layer of a conductive material that has a comparatively high electrical resistance. Because of the comparatively high electrical resistance, the amount of heat developed in this layer is negligibly small but the layer is still capable of shielding the electrical connection conductor from the RF field nevertheless.

Even though it usually is not annoying that the housing is visible in the MRI image during the maneuvering with the invasive device, when such known shielding is used it may occur that the housing is also visible in the ultimate MRI image to be formed; such a presence is undesirable for some applications.

It is an object of the invention to provide an invasive device of the kind set forth where the distal end is visible in an MRI image, where heating of the electrical connection conductor by the RF field is avoided, and where the envelope is completely invisible in the MRI image.

To this end, the invasive device in accordance with the invention is characterized in that the connection conductor comprises mutually separated segments, each of which is shorter than a predetermined value, and that the separation between the segments is realized by way of frequency-dependent separating elements that constitute a conductor for LF currents and an isolator for RF alternating current.

When a predetermined value is chosen for the length of the segments of the connection conductor, that is, a length that is shorter than the wavelength of the RF field in the MRI apparatus, practically no induction of currents can occur in the connection conductor, so that heat cannot be developed therein. Moreover, the connection conductor itself will not exert a disturbing effect on this field either, so that it will not be visible in the MRI image. When the separation between the segments is realized by way of frequency-dependent separating elements that constitute a conductor for LF currents and an isolator for RF alternating current, the circuit that is arranged at the distal end can be supplied with an LF current (for example, a direct current) via the connection conductor, so that at option this circuit can be rendered visible or not visible in an MRI image. It is alternatively possible to choose this circuit to be such that it can also perform other functions, such as illumination or a physiological sensor function.

If suitable visibility is desired, a coil that is at option traversed or not traversed by direct current can be used for this circuit. Such a direct current locally distorts the homogeneous magnetic field; this disturbance becomes manifest in the MRI image as a recognizable image deviation that can be used as an indicator for the circuit. This indicator can be simply deactivated by switching off the direct current during the acquisition of the ultimate MRI image.

In one embodiment of the invention the predetermined value of the length of the segments is less than 120 cm. This length is based on the customary situation where the homogeneous magnetic field has a strength of 1.5 Tesla; the frequency of the RF field then amounts to 64 MHz, the wavelength of this field then being approximately 4.6 m. The length of the segments of 120 cm then corresponds to ¼ wavelength; in practice this value usually suffices to achieve the desired effect in accordance with the invention.

The predetermined value for the length of the segments in a preferred embodiment in accordance with the invention is less than 24 cm. It has been found in practice that in practically all circumstances this choice of the length of the segments suffices to realize the desired effect in accordance with the invention.

In a further embodiment of the invention the separating elements are formed by self-inductances that do not contain a ferromagnetic material. As a result of this step it is avoided that the field concentration in the self-inductance elements has an undesirable effect on the homogeneity and/or the strength of the homogeneous field that is generated by the MRI apparatus.

The self-inductances in another embodiment in accordance with the invention are formed in that the input core and the output core in the connection conductor are wound so as to form bifilar coils. As a result of this step it is avoided that the input core and the output core in the connection conductor generate a field outside the self-inductance elements that would have an adverse effect on the homogeneity and/or the strength of the homogeneous field that is generated by the MRI apparatus.

The segments in another embodiment in accordance with the invention are formed by mutually twisted cores. As a result of this step it is again avoided that the input core and the output core in the connection conductor generate a field that would have an adverse effect on the homogeneity and/or the strength of the homogeneous field that is generated by the MRI apparatus.

The self-inductances in another embodiment in accordance with the invention have a value of at the most 1 μH. It has been found in practice that this choice of the value of the self-inductances suffices to realize the desired separation between the segments while nevertheless such small dimensions of the self-inductances are possible that these elements can be provided in a housing of, for example, a catheter.

The invention also relates to an MRI apparatus that is arranged to co-operate with the invasive device in accordance with the invention. The MRI apparatus is provided with a power supply unit for applying electrical energy to the circuit via the connection conductor, and with switching means for interrupting the supply of electrical energy to the circuit as desired. The attendant staff can decide to make the device visible in the MRI image by applying electrical energy to the circuit in the invasive device or not. This is important, for example when the device is constructed as a catheter, that is, during the positioning of the catheter in the body of the patient to be treated. When the catheter has reached its ultimate position, the catheter can be made invisible in the MRI image by switching off the electrical energy, so that the catheter does not disturb the image to be ultimately formed.

The switching means may notably be arranged to interrupt the supply of electrical energy to the circuit in response to an execution signal for the execution of an MRI exposure by the MRI apparatus. This step enables automatic execution of the described procedure. Moreover, this step offers the advantage that the device is invisible only for a brief period of time, that is, during the formation of the actual MRI image, and that it can be permanently observed during the remaining time.

Figure 2:
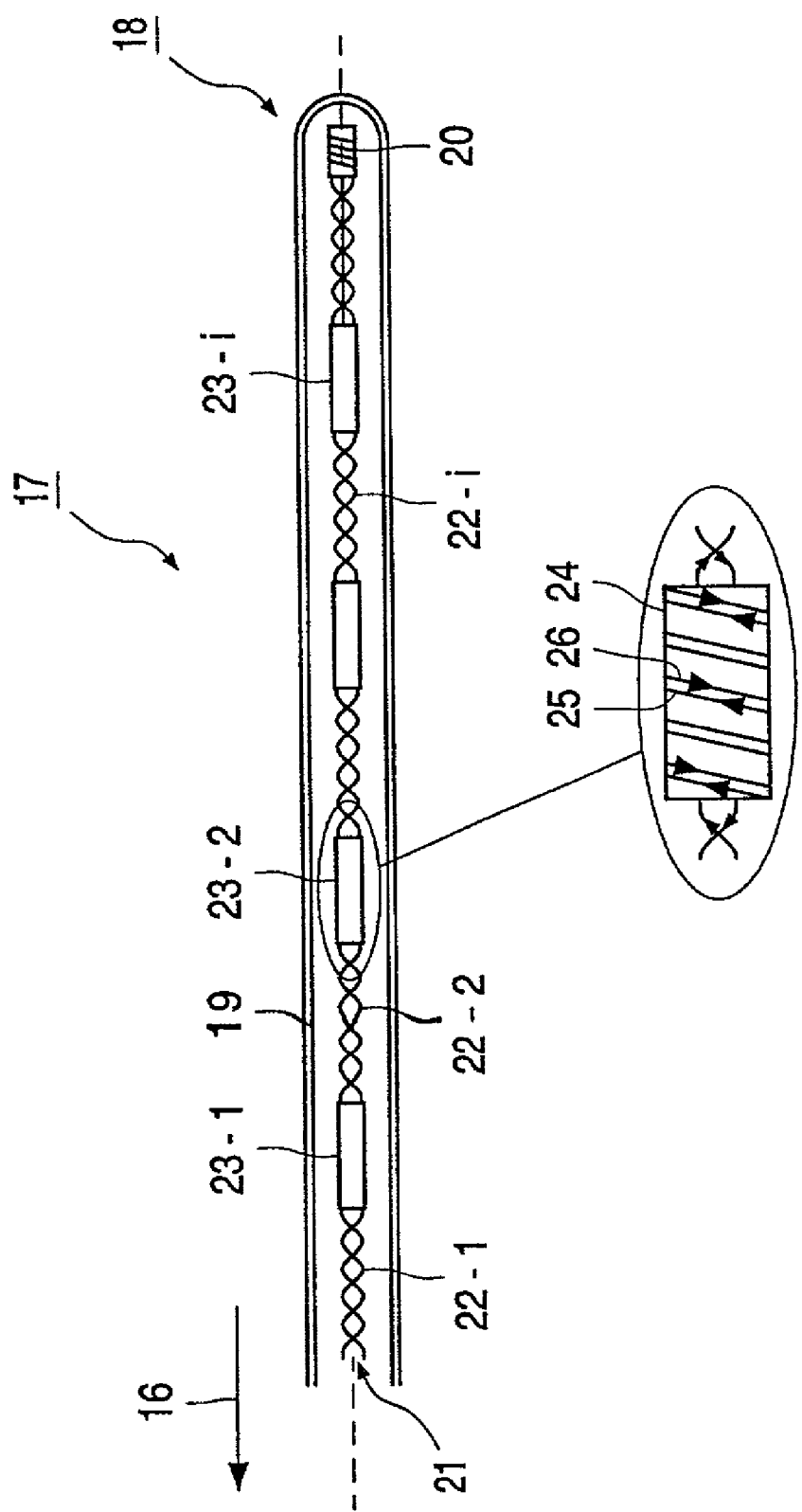

The invention will be described in detail hereinafter with reference to the Figures in which corresponding reference numerals denote corresponding elements. Therein:

FIG. 1 shows diagrammatically the general construction of a known magnetic resonance apparatus, and FIG. 2 shows an embodiment of the invasive device in accordance with the invention that is provided with a connection conductor in accordance with the invention that is intended for connection to a circuit in the invasive device and is provided with self-inductance elements.

FIG. 1 shows an apparatus for imaging by means of magnetic resonance (MRI). The apparatus includes a first magnet system 2 for generating a homogeneous, static magnetic field. The z direction of the co-ordinate system shown corresponds as usual to the direction of the static magnetic field. The MRI apparatus includes a plurality of gradient coils 3, 4 and 5 for generating further magnetic fields that have a gradient in the x, the y, and the z direction. The gradient coils 3, 4 and 5 are fed by a power supply unit 11. The magnet system 2 encloses an imaging volume that is large enough to accommodate a part of an object to be examined, for example a patient 7. An RF transmitter coil 6 serves to generate RF fields and is connected, via a transmission and receiving circuit 9, to an RF transmitter and modulator 8. The RF transmitter coil 6 is arranged around or on a part of the patient 7 in the imaging volume. There is also provided a receiving coil which is connected to a signal amplifier and demodulation unit 10 via the transmission and receiving circuit 9. The receiving coil may be the same coil as the transmitter coil 6. A control unit 12 controls the modulator 8 and the power supply unit 11 in order to generate special pulse sequences that contain RF pulses and gradient pulses. After the excitation of spins by means of RF pulses in the body to be imaged that is situated in the imaging volume, an MRI signal can be received by means of the receiving coil 6. The information of the magnetic resonance signal that is derived from the demodulation unit 10 is applied to a processing unit 14. The processing unit 14 processes the information so as to form an image by transformation, which image can be displayed on a monitor 15. FIG. 1 also shows an invasive device in accordance with the invention in the form of a catheter 17 that can be introduced into the patient 7, and also a catheter control unit 16. The catheter 17 will be described in greater detail with reference to FIG. 2.

FIG. 2 shows an invasive device in accordance with the invention in the form of a catheter 17. The catheter comprises a distal end 18 and a housing 19 that is connected to the distal end 18. A circuit 20 is provided at the distal end 18. The circuit 20 in the embodiment that is shown in FIG. 2 is formed as a coil where through an LF current can be conducted. However, it is to be noted that the circuit 20 may have a variety of other appearances, for example, a light source for illumination in the case of internal observation or for internal treatment, or a sensor circuit for the measurement of physiological quantities.

An electrical connection conductor 21 that is connected to the circuit 20 extends through the housing 19 for the transport of (DC) power supply energy and/or LF signals. In this context LF signals are to be understood to mean signals of a frequency that is substantially lower than the frequency of the RF field that is used in the MRI apparatus, for example, 64 MHz. This low frequency should be so low that the conductance by the connection conductor 21 can take place practically without interference and that this low frequency does not have a disturbing effect on the RF field. The desired effect of an unimpeded transport of LF signals without exerting a disturbing effect on the RF field is achieved in that the connection conductor 21 consists of mutually separated segments 22-$i$, each of which is shorter than ¼ of the wavelength of said RF field of the MRI apparatus, that is, preferably shorter than ¹⁄₂₀ of said wavelength.

The separation between the segments is realized by means of self-inductance elements 23-1, 23-2, 23-$i$. As is known, self-inductance elements are frequency-dependent separating elements that constitute a conductor for low-frequency currents and an isolator for RF alternating current. The frequency used for the RE field that is generated by the coils 6 is of the order of magnitude of some tens of MHz and typically amounts to, for example 64 MHz. This frequency corresponds to a wavelength of approximately 469 cm, so that the segments 22-$i$ have a length of approximately 469/20≈23 cm. Said segments are constructed in the form of two cores that are twisted around one another; this has the effect that the power supply current that flows through these cores generates a magnetic field that cannot be noticed outside the supply conductor and that no current (or only a negligibly small current) is induced therein by said field.

FIG. 2 is a more detailed representation of a self-inductance element 23-$i$. The self-inductance elements 23-$i$ are constructed as coils that are wound on a carrier 24 that does not interact with the RF field and with the homogeneous B field, so that this carrier cannot disturb said fields and cannot be influenced thereby itself. A suitable material for this coil carrier is, for example polycarbonate. The two cores 25 and 26 of the connection conductor 21 are wound on the carrier 24 in such a manner that the magnetic fields generated by the current in these cores compensate one another to a high degree, so that these coils do not generate a noticeable field. This effect is achieved by arranging the two cores directly adjacent one another on the carrier in such a manner that the currents in these two cores oppose one another. This is referred to as a bifilar winding. A further effect of the bifilar winding is that the RF field cannot generate currents in the connection conductor because the self-inductance has a high impedance for such currents (which would occur in the common mode, meaning that such currents would have the same direction in the two cores 25 and 26). The effect of said choice of the length of the segments, separated by self-inductances that have a high impedance for said RF frequency, is that these segments cannot take up energy from the RF field and hence can neither be heated by said field nor disturb said field to any noticeable extent.

It has been found that it is possible to realize a self-inductance of 0.5 $\mu$H; in that case the self-inductance element has a thickness of 1.8 mm and a length of 13 mm. For this purpose use is made of 66 bifilar turns of a wire of a thickness of 0.1 mm. A self-inductance of such dimensions can be introduced into the housing of a commonly used catheter that is known by the name 6 French. When these self-inductances are spaced 20 cm apart, the connection conductor will not be heated and there will be no annoying interference with the homogeneous magnetic field and the RF field of the MRI apparatus.

What is claimed is:

1. An invasive device (17) that is intended to be introduced into an object (7) that is to be imaged by means of an MDI apparatus, said invasive device comprising a distal end (18) and is provided with a housing (19) that extends to the distal end, with a circuit (20) that is arranged at the area of the distal end, and also with an electrical connection conductor (21) that is connected to the circuit and extends through the housing, the connection conductor (21) comprises mutually separated segments (22-$i$), each of which is shorter than a predetermined value, and that the separation between the segments is realized by way of frequency-dependent separating elements (23-$i$) constructed as cores (25, 26) wound on a carrier (24) in such a manner that magnetic fields generated by current in the cores (25, 26) compensate one another, said elements (23-$i$) constitute a conductor for LF currents and an isolator for RF alternating current.

2. An invasive device as claimed in claim 1, wherein the predetermined value for the length of the segments (22-$i$) is less than 120 cm.

3. An invasive device as claimed in claim 2, wherein the predetermined value for the length of the segments (22-$i$) is less than 24 cm.

4. An invasive device as claimed in claim 1, wherein the separating elements are formed by self-inductances that do not contain a ferromagnetic material.

5. An invasive device as claimed in claim 4, wherein the self-inductances are formed in that the cores (25, 26) of the connection conductor (21) are wound so as to form bifilar coils.

6. An invasive device as claimed in claim 4, wherein the self-inductances have a value of at the most 1 $\mu$H.

7. An invasive device as claimed in claim 1, wherein the segments are formed by mutually twisting the cores (25, 26).

* * * * *